United States Patent
Klingseis et al.

(10) Patent No.: US 8,328,814 B2
(45) Date of Patent: Dec. 11, 2012

(54) SURGICAL GUIDING INSTRUMENT

(75) Inventors: Susanne Klingseis, Neu-Ulm (DE); Kay Fischer, Tuttlingen (DE); Uwe Mattes, Tuttlingen (DE)

(73) Assignee: Aesculap AG, Tuttlingen (DE)

( * ) Notice: Subject to any disclaimer, the term of this patent is extended or adjusted under 35 U.S.C. 154(b) by 785 days.

(21) Appl. No.: 12/123,116

(22) Filed: May 19, 2008

(65) Prior Publication Data

US 2008/0312705 A1 Dec. 18, 2008

Related U.S. Application Data

(63) Continuation of application No. PCT/EP2006/068367, filed on Nov. 11, 2006.

(30) Foreign Application Priority Data

Nov. 24, 2005 (DE) .......................... 10 2005 056 818

(51) Int. Cl.
*A61B 17/58* (2006.01)
(52) U.S. Cl. ...................... 606/99; 623/17.11; 606/86 A
(58) Field of Classification Search .................. 606/79, 606/80, 86, 87, 90, 96, 99, 914; 623/17.11
See application file for complete search history.

(56) References Cited

U.S. PATENT DOCUMENTS

| | | | |
|---|---|---|---|
| 4,586,497 A | 5/1986 | Dapra et al. | |
| 4,653,509 A | 3/1987 | Oloff et al. | |
| 6,342,057 B1 * | 1/2002 | Brace et al. | 606/96 |
| 2002/0161446 A1 | 10/2002 | Bryan et al. | |
| 2003/0032962 A1 * | 2/2003 | McGahan et al. | 606/80 |
| 2003/0135277 A1 * | 7/2003 | Bryan et al. | 623/17.12 |
| 2004/0002711 A1 * | 1/2004 | Berry | 606/79 |
| 2004/0143332 A1 | 7/2004 | Krueger et al. | |
| 2004/0215198 A1 | 10/2004 | Marnay et al. | |
| 2005/0059976 A1 * | 3/2005 | Bryan et al. | 606/80 |
| 2005/0113842 A1 * | 5/2005 | Bertagnoli et al. | 606/90 |

FOREIGN PATENT DOCUMENTS

| | | |
|---|---|---|
| DE | 100 03 967 | 8/2001 |
| WO | WO 98/04202 | 2/1998 |
| WO | WO 02/11633 | 2/2002 |
| WO | WO 2004/019785 | 3/2004 |

OTHER PUBLICATIONS

PCT Written Opinion Containing Cited References for PCT/EP2006/068367 Completed Jul. 17, 2008.

* cited by examiner

*Primary Examiner* — Thomas Barrett
*Assistant Examiner* — Melissa A Golob
(74) *Attorney, Agent, or Firm* — RatnerPrestia

(57) ABSTRACT

A surgical guiding instrument for a surgical machining tool has a substantially elongated instrument body having a proximal end and a distal end and defining a longitudinal axis. The instrument body carries a guiding device for the machining tool that can be used in minimally invasive surgery. The guiding device is arranged and constructed so as to enable the machining tool to be positively guided by it along a path of movement defined by the guiding device. The path of movement corresponds to a superimposed translational-pivotal movement.

45 Claims, 5 Drawing Sheets

SURGICAL GUIDING INSTRUMENT

CROSS-REFERENCE TO RELATED APPLICATIONS

This application is a continuation under 35 U.S.C. §365 of international application number PCT/EP2006/068367, filed on Nov. 11, 2006, which claims priority to German application number 10 2005 056 818.1, filed Nov. 24, 2005. The contents of both applications are incorporated by reference herein in their entirety and for all purposes.

FIELD OF THE INVENTION

The present invention relates to surgical guiding instruments generally, and more specifically to a guiding instrument for a surgical machining tool which is configured for machining vertebral bodies.

BACKGROUND OF THE INVENTION

Surgical guiding instruments are used to guide surgical chisels or surgical milling tools for machining bones or parts of bones of the body of a human being or an animal. The instruments primarily serve the purpose of preventing the machining tool from having to be held freely by an operator. Such a procedure harbors disadvantages, particularly when operations are performed in the area of the vertebral column, as this involves a high risk of injuring nerve paths running in or out of the vertebral canal. Owing to their structural shape and size, known surgical guiding devices are unsuitable for guiding surgical machining tools in minimally invasive surgery. In addition, known surgical guiding devices are unsuitable because the guiding instrument and machining tool severely obstruct the view of the operating site.

An object underlying the present invention is, therefore, to improve a surgical guiding instrument that can be used, in particular, in minimally invasive surgery.

SUMMARY OF THE INVENTION

In a first aspect of the invention, a surgical guiding instrument for a surgical machining tool is configured for machining vertebral bodies and has a distal tool end. The guiding instrument includes a substantially elongated instrument body having a proximal and a distal end and defines a longitudinal axis. The instrument body carries a guiding device for the machining tool, wherein the guiding device is arranged and constructed so as to enable the machining tool to be positively guided along a path of movement defined by the guiding device. The path of movement corresponds to a superimposed translational-pivotal movement.

In a second aspect of the invention, surgical instrumentation includes at least one surgical machining tool configured for machining vertebral bodies and at least one surgical guiding instrument. The guiding instrument includes a substantially elongated instrument body having a proximal end and a distal end, and defines a longitudinal axis. The instrument body carries a guiding device for the machining tool, wherein the guiding device is arranged and constructed so as to enable the machining tool to be positively guided along a path of movement defined by the guiding device. The path of movement corresponds to a superimposed translational-pivotal movement.

BRIEF DESCRIPTION OF THE DRAWING FIGURES

The foregoing summary and the following description may be better understood in conjunction with the drawing figures, of which.

DETAILED DESCRIPTION OF PREFERRED EMBODIMENTS OF THE INVENTION

Although the invention is illustrated and described herein with reference to specific embodiments, the invention is not intended to be limited to the details shown. Rather, various modifications may be made in the details within the scope and range of equivalents of the claims and without departing from the invention.

The present invention relates to a surgical guiding instrument for a surgical machining tool which is configured for machining vertebral bodies and has a distal tool end. The guiding instrument comprises a substantially elongated instrument body having a proximal and a distal end and defining a longitudinal axis, and the instrument body carries a guiding device for the machining tool. Surgical guiding instruments in accordance with the present invention feature a guiding device that is arranged and constructed so as to enable the machining tool to be positively guided along a path of movement defined by the guiding device. The path of movement corresponds to a superimposed translational-pivotal movement.

Guiding instruments in accordance to preferred embodiments of the invention have the advantage that the machining tool can be pivoted at least partly out of the operating site by the specially constructed guiding device, so that an operator's view of the operating site is significantly improved. In particular, such a guiding device opens up the possibility of guiding the machining tool in such a way that, if it comprises a grip part, the latter is movable outside of the operating site and the viewing area of the operating site during practically the entire machining procedure.

In order that, for example, straight-lined grooves or recesses can be prepared with the machining tool, it is expedient for the guiding device to be arranged and constructed so as to enable a tip or a center of the distal tool end to be positively guided by it along a linear path curve. This means that, for example, a spherical rotating tip of a milling tool is movable with its center along a straight line or a straight portion, with the machining tool simultaneously executing both a translational movement and a pivotal movement. However, the guiding device may, of course, also be constructed so as to enable a tip or a center of the distal tool end to be positively guided along an optional path curve which, in particular, is curved once or several times.

In order that an operator need not hold the machining tool during the entire surgery, it is advantageous for the guiding device to comprise a holder for the machining tool. In principle, it is conceivable for the holder to be constructed as part of the machining tool. However, in order that both the guiding instrument and the machining tool are optimally cleanable, it is advantageous for the holder to be releasably connectable to the machining tool.

A particularly simple design of the guiding instrument is obtained when the holder comprises a clamping device for clamped connection to a machining tool. For example, the clamping device may comprise two clamping jaws between which the machining tool is clampable. As an alternative, clamping by means of a pipe clip-like component is also possible.

In accordance with a preferred embodiment of the invention, provision may made for the guiding device to comprise a first guiding element defining a pivot axis for the machining tool, so that the machining tool is displaceable relative to the first guiding element and is pivotable about the pivot axis. Independently of how the guiding device is otherwise constructed, in particular, a superimposed translational-pivotal movement can be prescribed for the machining tool with the first guiding element. The first guiding element preferably defines the pivot axis.

The handling of the guiding instrument and a machining tool guided thereon is further simplified by the machining tool or a part thereof being displaceably and pivotably mountable on the first guiding element. Optimal guidance and, at the same time, minimal structural size of the guiding instrument can be achieved by the first guiding element being arranged at the distal end or in the area of the distal end of the instrument body.

To define a pivotal movement with the first guiding element in a simple way, the first guiding element expediently has in relation to a plane containing the longitudinal axis a convexly curved guide surface. This allows a portion of the machining tool abutting on the guide surface to both slide and roll thereon. A combination of both movements results in a superimposed translational-pivotal movement of the machining tool.

To achieve optimal guidance in a plane intersecting the longitudinal axis, the guide surface is advantageously concavely curved in the plane intersecting the longitudinal axis in the direction towards the longitudinal axis. A particularly good positive guidance is achieved for the machining tool by the first guiding element comprising a guide sleeve with a guide through-hole for the machining tool or a part, in particular a shaft, thereof. Owing to the guide sleeve, the machining tool can carry out a translational movement and/or a pivotal movement with positive guidance.

The design of the guiding instrument is further simplified when the guide through-hole comprises an inner wall surface, and when the inner wall surface forms the guide surface. In particular, the guide surface may be convexly curved and thereby point in the direction towards a longitudinal axis of the guide through-hole.

The stability of the guiding instrument is further improved when the guiding device comprises a second guiding element for holding and guiding the machining tool on the instrument body, and when the machining tool is mountable for sliding displacement and pivotal movement relative to the second guiding element. The first and second guiding elements together form an optimal guiding device for a machining tool, which is easy for an operator to handle.

To enable an operator to move the machining tool particularly easily with the aid of the guiding instrument, the machining tool or a part thereof is advantageously mountable for sliding displacement on the second guiding element and pivotal movement about the pivot axis. Guidance of the machining tool with a high degree of precision is achievable by the second guiding element being arranged at the proximal end or in the area of the proximal end of the instrument body. In particular, it is desirable for a spacing of the two guiding elements from each other to be maximally large.

The machining tool can be guided with the guiding instrument in a particularly simple way when the second guiding element comprises at least one first guiding member for guiding the machining tool or a part thereof along a curve defined by the second guiding element. For example, the guiding member may be in the form of a recess or a projection.

It is particularly advantageous when the second guiding element comprises at least one guiding body, and when the at least one first guiding member is in the form of a guide groove arranged on the at least one guiding body. For example, a projection on the machining tool or on a holder for the latter can thus be guided in the guide groove. The guide groove itself can be straight-lined or curved, so that on account of the shape and prescribable direction of the guide groove, a translational-pivotal movement is prescribable in a simple way for the machining tool.

The design of the guiding instrument is even simpler when two symmetrically arranged guiding bodies are provided. For example, these may be so constructed that guide grooves provided thereon point towards each other, so that laterally protruding projections on the machining tool or on a holder for the machining tool can enter into the guide grooves. It is also conceivable to provide four guiding bodies so as to form a second guiding device on the guiding instrument.

The at least one guiding body expediently comprises two or more guide grooves. This enables an operator to perform different translational-pivotal movements with the machining tool with positive guidance, and opens up the possibility for him to, for example, machine a bone in different ways without a further instrument being required therefor.

The at least one first guiding member is advantageously inclined relative to the longitudinal axis. For example, a guide groove inclined relative to the longitudinal axis can prevent unnecessary restriction of the view of an operating site.

It is expedient for the holder to comprise at least one second guiding member, and for the at least one second guiding member to be constructed so as to be movably mounted on the first guiding member. Such a design of the holder has the advantage that a safe guidance of any machining tools is possible with the aid of the holder on the guiding instrument.

A particularly simple design of the guiding instrument is achievable by the at least one second guiding member being a guiding projection which protrudes transversely or substantially transversely to the longitudinal axis and is shaped so as to enter into the at least one guide groove. For example, the guiding projection may be in the form of a short cylindrical pin. This design additionally enables the guiding projection to be displaced in a guide groove and also pivoted relative thereto.

The second guiding element is expediently arranged in spaced relationship to the first guiding element in the longitudinal direction. The greater the spacing of the two guiding elements from each other, the more precisely can a machining tool be guided.

In addition, in order to enable path curves for a translational-pivotal movement to be optionally prescribed, it may advantageously be provided that a spacing between the first and second guiding elements is alterable.

In accordance with a preferred embodiment of the invention, it may be provided that the first and second guiding elements are arranged relative to each other and coordinated with each other such that a distal end of a machining tool is movable along a straight or substantially straight line parallel or substantially parallel to the longitudinal axis. This configuration enables a straight-lined groove or a recess to be formed on a bone, for example, on a vertebral body, with the aid of the guiding instrument and a machining tool guided thereon.

To enable placement of the guiding instrument in a defined manner on a vertebral body, in particular, for preparation thereof prior to insertion of an intervertebral implant into an intervertebral space between adjacent vertebral bodies, it is expedient for an implant body for insertion into the intervertebral space between adjacent vertebral bodies of the vertebral column of a human being or an animal to be provided at the distal end of the instrument body, and for the implant body to comprise two contact surfaces adapted for placement on the vertebral bodies. In particular, it is thus possible to insert the implant body into the intervertebral space and to machine one or both adjacent vertebral bodies in a desired manner with a machining tool that is positively guided on the guiding instrument.

To enable the guiding instrument to be cleaned with particular ease, it is expedient for the implant body to be releasably connectable to the instrument body. In addition, this has the advantage that different implant bodies can be connected to the instrument body, so that the guiding instrument is universally employable for the entire vertebral column.

In order that adjacent vertebral bodies can be held in a desired natural position for machining thereof, it is advantageous for the contact surfaces to be inclined relative to each other about an angle of inclination. The adjacent vertebral bodies can thus be machined in a position which corresponds to that after insertion of an intervertebral implant.

In accordance with a preferred embodiment of the invention, it may be provided that a set of implant bodies is provided, and that the implant bodies of the set have a different size and/or a different angle of inclination of the contact surfaces relative to each other and/or a different spacing of the contact surfaces from each other. Such a set of implant bodies makes it possible to manage with only one instrument body and to nevertheless use the guiding instrument for preparing different patients and different intervertebral spaces.

An additional guidance for the machining tool may be provided in a simple way by at least one guide groove being arranged in one of the two contact surfaces on the implant body so as to extend parallel or substantially parallel to the longitudinal axis of the instrument body. In particular, both contact surfaces may be provided with guide grooves.

To prevent the guiding instrument from being inserted too deeply into the body of a human being or an animal, in particular, into an intervertebral space thereof, it is advantageous for a stop device to be provided for limiting a penetration depth of the implant body into the intervertebral space.

A stop device which is particularly simple to operate and easy to manufacture comprises at least one projection protruding transversely or substantially transversely to the longitudinal axis of the instrument body. Such a projection prevents the instrument from being able to be moved further in the direction towards the vertebral body once the projection contacts or strikes the vertebral body.

The stop device is preferably releasably connectable to the implant body or to the instrument body. This makes it possible to remove the stop device, for example, when it is not required or when the view of the operating site is particularly severely restricted by the stop device. In addition, the guiding instrument can thus be disassembled in a simple way for cleaning purposes.

A particularly simple design of the stop device is achieved by the stop device comprising a carrier and by the implant body or the instrument body comprising a guiding device for the carrier for guiding a movement of the carrier relative to the instrument body and/or to the implant body parallel or substantially parallel to the longitudinal axis.

To enable the stop device or parts thereof to be moved in a defined way, it may advantageously be provided that the guiding device comprises at least one guiding bar protruding in proximal direction on the implant body, and that the carrier is displaceably mounted on the at least one guiding bar.

In order that a position of the stop device is prescribable in a defined way, it is expedient for the stop device to comprise a stop member, and for a spacing between the stop member and the carrier to be alterable. The at least one projection can be moved in a simple way relative to the guiding instrument and/or to the implant body and can, therefore, prescribe a penetration depth for the guiding instrument when the carrier carries the at least one projection. Furthermore, the guiding instrument can be held particularly well when a grip part is provided at the proximal end of the instrument body.

To enable an operator to use grip parts preferred by him, it is advantageous for the grip part to be releasably connectable to the instrument body. Furthermore, the instrument can thus be cleaned very well in a simple way. In order not to additionally obstruct the view of the operating site, it is expedient for the grip part and the instrument body to extend at an angle relative to each other. Both the construction and the manufacture of the guiding instrument are simplified when the guiding instrument is constructed mirror-symmetrically in relation to a mirror plane containing the longitudinal axis.

The object set forth at the outset is further accomplished, in accordance with the invention, with surgical instrumentation, comprising at least one surgical machining tool which is configured for machining vertebral bodies and has a distal tool end, and at least one surgical guiding instrument for the at least one surgical machining tool, the guiding instrument comprising a substantially elongated instrument body having a proximal and a distal end and defining a longitudinal axis, and the instrument body carrying a guiding device for the machining tool, in that the guiding device is arranged and constructed so as to enable the machining tool to be positively guided by it along a path of movement defined by the guiding device, and in that the path of movement corresponds to a superimposed translational-pivotal movement. With such instrumentation, parts of the human body, for example, bones, in particular, vertebral bodies, are easily and reliably machinable in a desired manner with a machining tool.

A bone, in particular, a vertebral body, can be machined with particular ease when the at least one machining tool is a milling tool with an elongated shaft, and when the distal tool end is a milling head that rotates. Such a machining tool can be positively guided in a simple and reliable manner with the guiding instrument, and a defined recess can thus be prepared in a bone.

Figure 1:
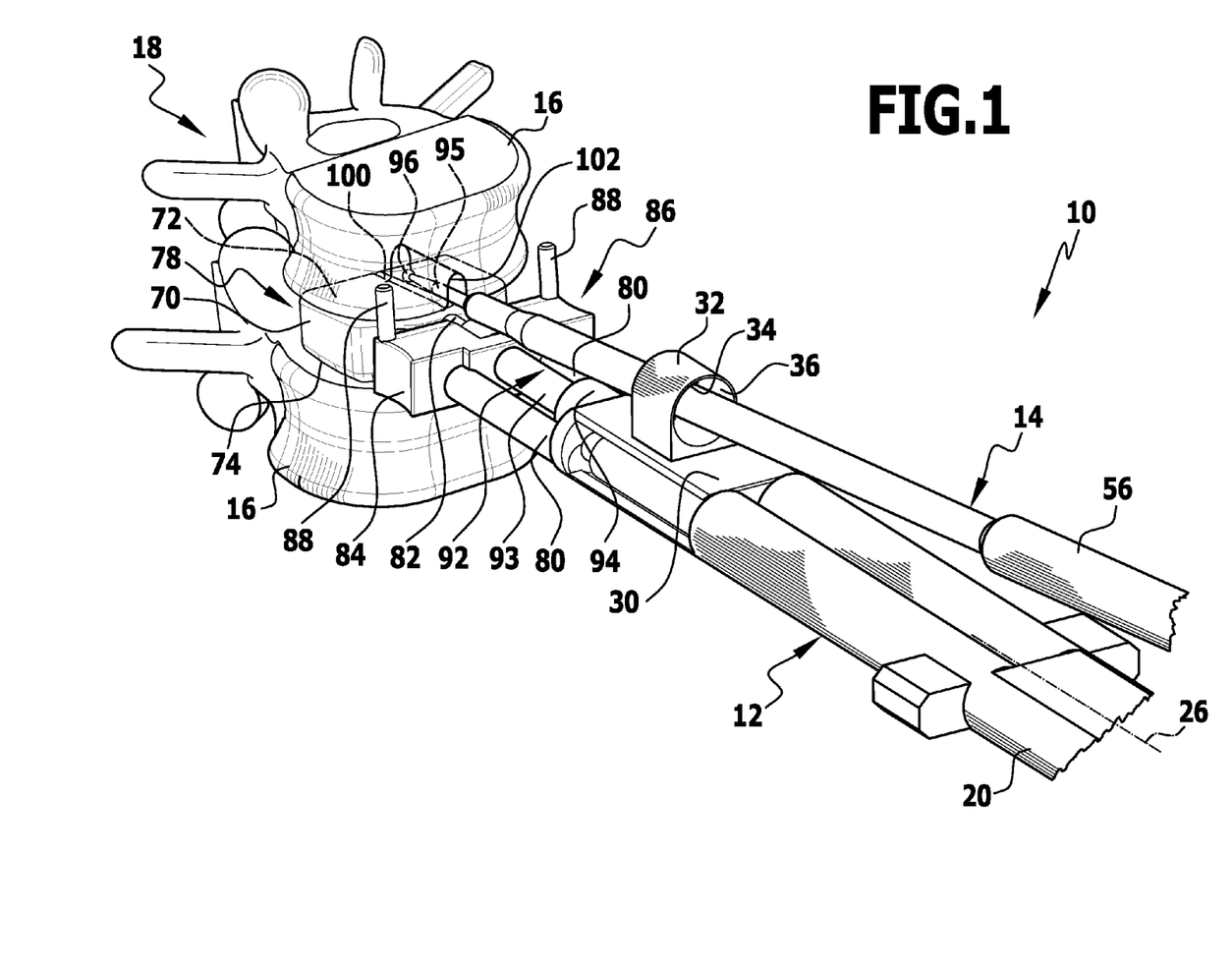
FIG. 1 is a perspective view of instrumentation according to one exemplary embodiment of the invention, schematically shown in the course of preparing a vertebral body, with a portion of the instrumentation truncated for clarity.
Figure 2:
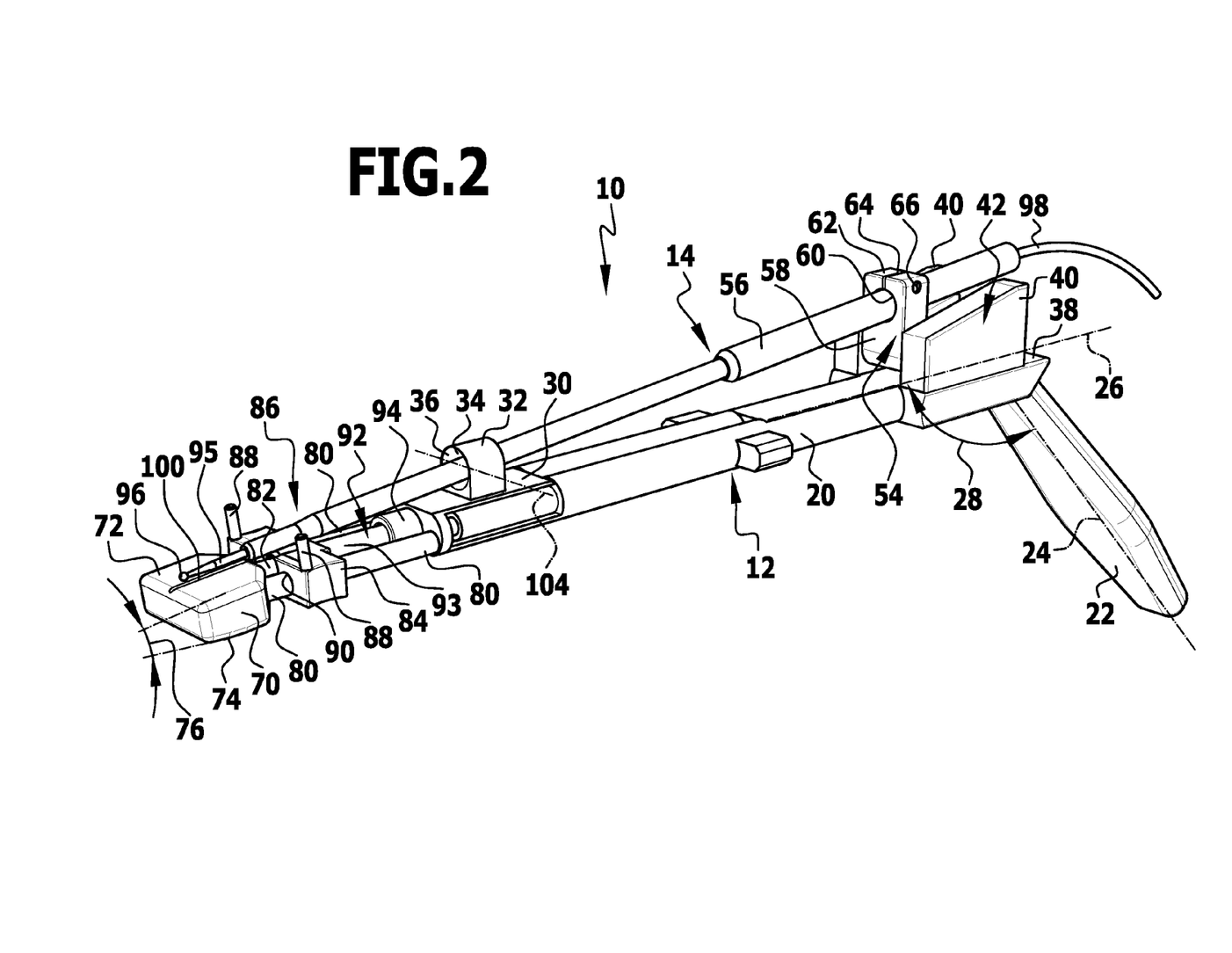
FIG. 2 is a perspective view of the instrumentation shown in FIG. 1.
Figure 3:
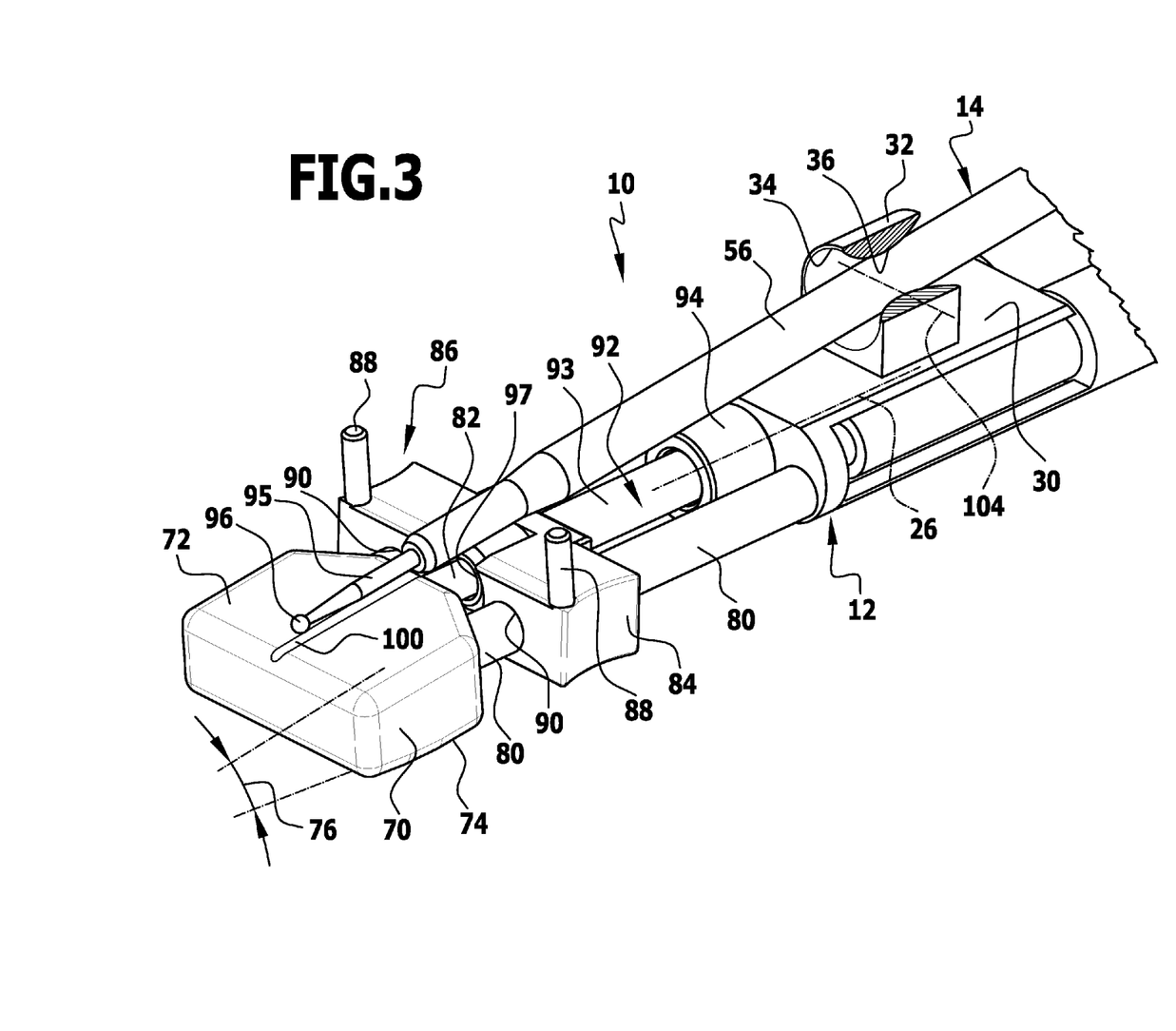
FIG. 3 is a truncated perspective view of a distal end of the instrumentation according to FIG. 1.
Figure 4:
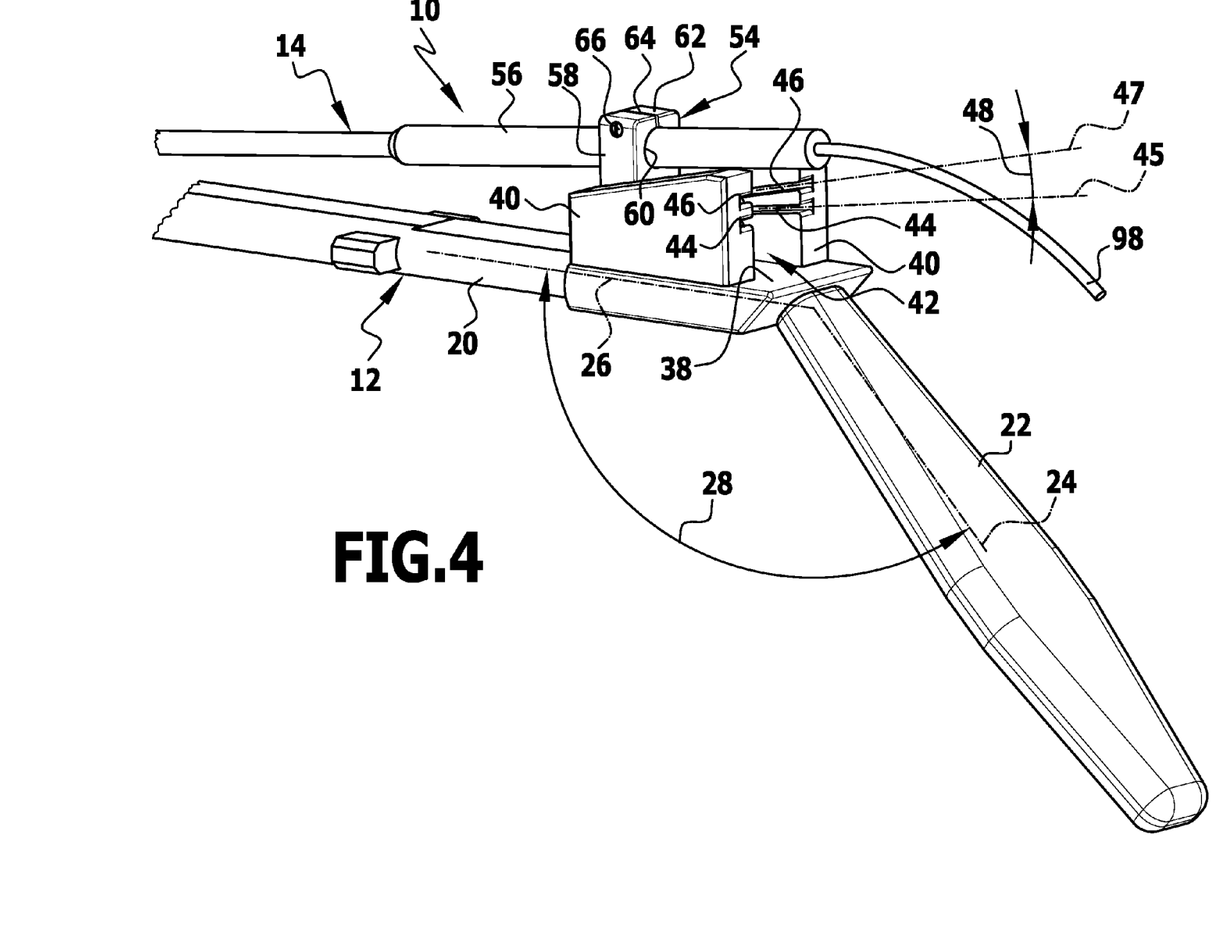
FIG. 4 is an enlarged truncated perspective view of a proximal end of the instrumentation according to the invention.
Figure 5:
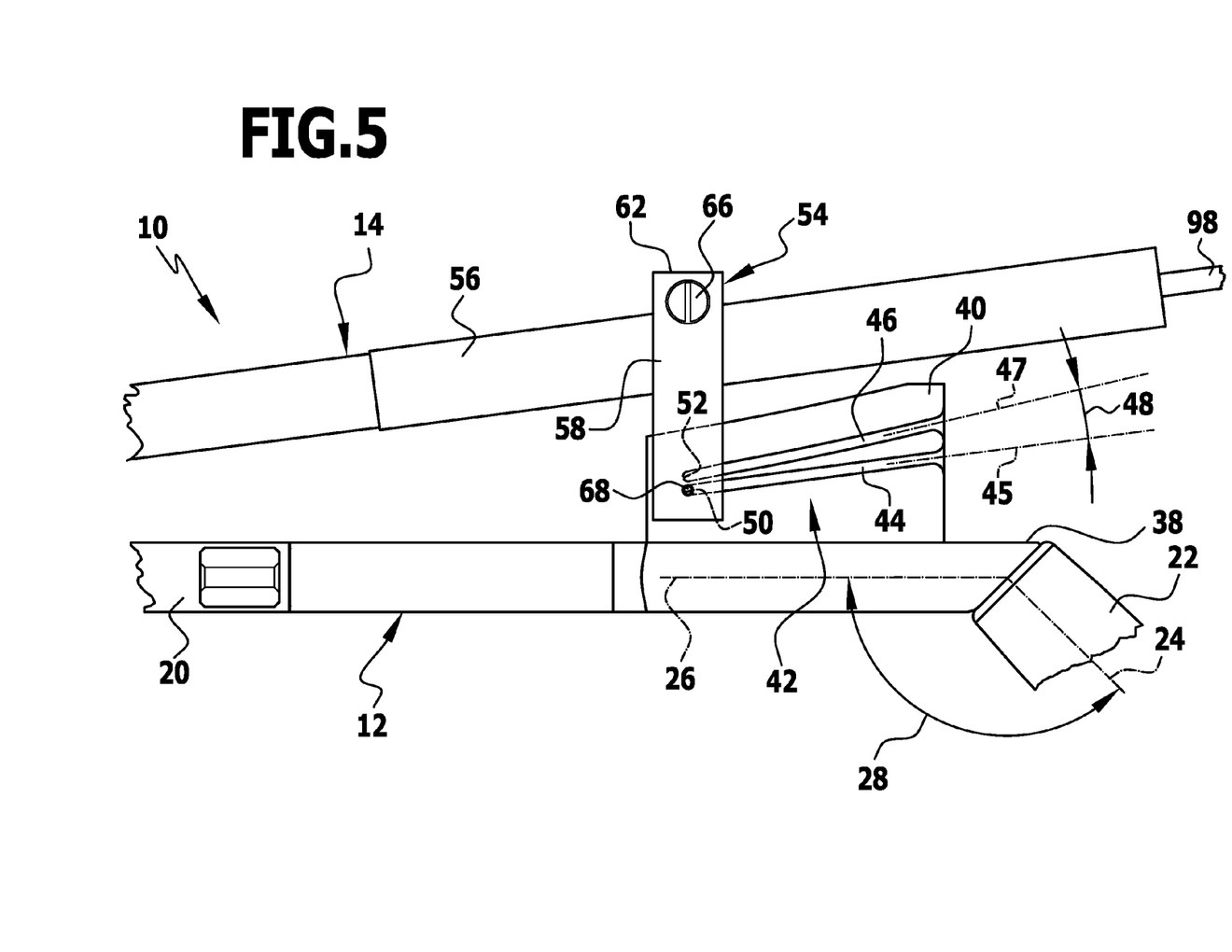
FIG. 5 is a side view of the proximal end of the instrumentation according to the invention, with portions of the instrumentation truncated for clarity.

The instrumentation depicted in FIGS. 1 to 5 and generally designated by reference numeral 10, comprising a surgical guiding instrument 12 and a surgical machining tool 14 in the form of a milling tool 14, serves, inter alia, as depicted in FIG. 1, to machine vertebral bodies 16 of the vertebral column 18 of a human being or an animal, as will be explained in further detail hereinbelow.

The guiding instrument 12 comprises an elongated instrument body 20 having a proximal and a distal end. Extending away from the proximal end is a handgrip 22 whose longitudinal axis 24 includes an obtuse angle 28 of approximately 135° with a longitudinal axis 26 of the instrument body 20. There is formed in the area of the distal end of the instrument body 20 a substantially cuboidal carrying element 30, which carries a first guiding element 32 in the form of a guide sleeve. The guide sleeve comprises a through-opening 34 extending substantially parallel to the longitudinal axis 26 and defining a convexly curved guide surface 36 pointing in the direction towards an axis of symmetry of the through-opening 34. In the guiding instrument 12 depicted in the Figures, the guiding element 32 is immovable relative to the instrument body 20. It is, however, also conceivable to arrange the guiding element 32 movably on the instrument body 20, for example, slidably parallel to the longitudinal axis 26. It is also possible to mount the guiding element 32 on the instrument body 20 so as to be slidable or pivotable in a plane orientated perpendicularly to the longitudinal axis 26.

There is provided in the area of the proximal end of the instrument body 20 a platform 38 which is arranged substantially parallel to the carrying element 30. The platform 38 carries two trapezoidal guide members arranged symmetrically in the form of bearing blocks 40, which jointly form a second guiding element 42. Each bearing block 40 comprises two guide grooves 44 and 46 whose longitudinal axes 45 and 47 are inclined relative to one another and include an angle of inclination 48 and are also inclined relative to the longitudinal axis 26. The guide grooves 44 and 46 extend along a straight line and are formed in the bearing blocks 40 so as to point in the direction towards the bearing block 40 respectively arranged mirror-symmetrically in relation to a plane of symmetry containing the longitudinal axis 26. A proximal end of the guide grooves 44 and 46 is open; a distal end thereof is closed and forms a stop 50 and 52, respectively.

The guiding instrument 12 further comprises a holder 54 for holding a shaft 56 of the milling tool 14 clamped. The holder 54 comprises a substantially cuboidal holding body 58 having a borehole 60 and a slot 64 connecting an end face 62 with the borehole 60. The generally clamp-like holder 54 further comprises a clamping screw 66, which is arranged in a borehole provided with an internal thread and arranged transversely to the slot 64, and which joins and can pull together the free ends of the holding body 58 that are separated by the slot 64, so that a diameter of the borehole 60 is somewhat reducible in size so as to hold the shaft 56 of the milling tool 14 clamped in the borehole 60.

Arranged on the holding body 58 substantially parallel to the clamping screw 66 are bearing pins 68 which protrude laterally in opposite directions and form second guide members which cooperate with the guide grooves 44 and 46 forming first guide members. The bearing pins 68 are configured so as to be insertable from the proximal direction into the guide grooves 44 and 46 and slidable therein, so that the holder 54 is mounted in its entirety for sliding displacement along the guide paths formed by the guide grooves 44 and 46 relative to the instrument body 20. The milling tool 14 held clamped on the holder 54, can, therefore, be moved in a defined manner relative to the instrument body 20 and mounted thereon.

The guiding instrument 12 further comprises an implant body 70 having two contact surfaces 72 and 74 which are inclined relative to each other about an angle of inclination 76. The implant body 70 is constructed for insertion into an intervertebral space 78 between two adjacent vertebral bodies 16. A set of implant bodies 70 is preferably provided, which vary in shape and size and have different angles of inclination 76 between the contact surfaces 72 and 74. This enables them to be optimally inserted into any of the intervertebral spaces of the vertebral column 18, which are all of different size and at which surfaces defined by the vertebral bodies 16 are inclined relative to one another to a different degree, so as to optimally fill the intervertebral space 78 originally filled by an intervertebral disc and to support the adjacent intervertebral bodies 16 relative to one another during the surgery.

Arranged on the implant body 70 are two protruding holding bars 80 extending parallel to each other and pointing in proximal direction. These are releasably connectable in a manner not shown in greater detail to the carrying element 30. This makes it possible to connect the instrument body 20, as required, to an implant body 70 that is optimally suited for the respective intervertebral space 78 to be machined.

Extending between the holding bars 80 parallel thereto is a short coupling pin 82 which is releasably connectable to a screw spindle 92 of a stop device generally designated by reference numeral 86. From a cuboidal carrier 84 extending transversely to the longitudinal axis there protrude two cylindrical projections 88 transversely to the longitudinal axis 26 and transversely to the carrier 84 and form stops for the vertebral bodies 16. The carrier 84 has two boreholes 90 through which the holding bars 80 can be pushed so that the carrier 84 is slidably mounted thereon.

A spacing between the carrier 84 and the implant body 70 can be varied by means of the screw spindle 92, which comprises a threaded section 93 extending in the direction of the longitudinal axis 26 and having an external thread, and a screw head 94 pointing in proximal direction and forming an actuating member. Arranged on the carrier 84 is a borehole which extends between the holding bars 80 and parallel thereto and has an internal thread. The threaded section 93 is screwed into the borehole. At its distal end, the threaded section 93 has a blind hole 97 which forms a rotary bearing for receiving the coupling pin 82. The screw spindle 92 is therefore mounted on the coupling pin 82 and held on the carrier 84. By rotating the screw spindle 92 held immovably in axial direction between the carrying element 30 and the coupling pin, the carrier can be moved in distal and proximal direction on the holding bars parallel to the longitudinal axis 26. The carrier 84 can be moved in proximal direction until its strikes the screw head 94, in distal direction until it strikes the implant body 70. A maximal spacing between the carrier 84 and the implant body 70 is defined by the position of the carrier 84 in which it strikes the screw head 94.

The milling tool 14 has a shaft which is rotatably mounted in the shaft 56 and terminates at the distal end in a spherical milling head 96. The shaft 56 tapers from its proximal end in the direction towards its distal end in several stages. Furthermore, the milling tool is driven by a drive, not shown in greater detail, which, for example, can be supplied with power via a connection cable 98. Alternatively, it is also conceivable to provide a rotatable, flexible drive shaft for driving the shaft 95 instead of the connection cable 98.

Use of the instrumentation 10 for preparing the vertebral bodies 16 will now be explained in greater detail. The guiding instrument 12 is made ready in preparation for the surgery. To do so, an implant body 70, which fills out in the desired manner the intervertebral space 78 between the vertebral bodies 16 to be machined is selected and connected to the instrument body 20. The implant body 70 preferably has a longitudinal groove 100 extending parallel or substantially parallel to the longitudinal axis 26 in one or both contact surfaces 72 and 74, respectively. The stop member 92 is set so that the projections 88 assume their most distal position, i.e., the carrier 84 then also assumes its most distal position in which a spacing between the implant body 70 and the carrier 84 is minimal.

A machining tool provided for machining the vertebral bodies 16, for example, the milling tool 14, is pushed with its shaft 56 through the borehole 60 of the holder 54 and clamped to the holder 54 by means of the clamping screw 66. The thus prepared milling tool 14 is pushed with its distal end to the fore, i.e., with the milling head 96, through the through-hole 34 of the guiding element 32. A minimal diameter of the through-hole 34 is only insignificantly larger than an outer diameter of the portion of the shaft 56 that is guided in the area of the first guiding element 32. The bearing pins 68 are then pushed into a respective one of the grooves 44 or 46 from the proximal direction, as a result of which the milling tool 14 is then movable in a defined manner relative to the guiding instrument 12. When the milling tool 14 is moved in distal direction it is positively guided along a path of movement which corresponds to a superimposed translational-pivotal movement. On the one hand, the shaft 56 of the milling tool 14 therefore slides translationally in the first guiding element 32, and, on the other hand, this translational movement is superimposed by a pivoting or rolling movement on the convexly curved guide surface 36. Owing to its construction, the guiding element 32 defines a pivot axis 104 about which the entire milling tool 14 is pivoted. Therefore, the milling head 96 also executes a superimposed translational-pivotal movement. The guide grooves 44 and 46 respectively, can, however, be constructed so that a center of the milling head 96 follows a straight-lined path. Consequently, the spherical milling head 96 also follows a generally straight-lined path. It is, of course also conceivable to construct the guide grooves 44 and 46 so that a center of the milling head 96 and, consequently, the milling head 96 itself follows a path which is curved once and/or several times.

To machine one or both vertebral bodies 16, before inserting the milling tool 14 through the guiding element 32, the implant body 70 connected to the instrument body 20 is inserted into the intervertebral space 78 until the projections 88 strike one of the vertebral bodies 16. The stop device 86 is then set so that the implant body 70 can be introduced to the desired penetration depth into the intervertebral space 78, a movement of the guiding instrument 12 in distal direction being, in turn, limited by the projections 88 striking a vertebral body 16. When the guiding instrument 12 finally assumes its desired position, the milling tool 14 is movably connected to the guiding instrument 12, as described hereinabove. To machine a groove 102 in the vertebral body 16, the milling head 96 is made to rotate and the milling tool 14 is moved in distal direction. In this way, the groove 102 is machined in a surface of the vertebral body 16 that points towards one of the contact surfaces 72 and 74, respectively. The groove 102 serves to receive a fin-like projection on an intervertebral implant, not shown, which can be inserted into the intervertebral space 78 after removal of the guiding instrument 12.

The view of the operating site is significantly improved by the generally somewhat inclined mounting of the milling tool 14 on the guiding instrument 12 and also by the handgrip 22 protruding laterally on the instrument body 20.

While preferred embodiments of the invention have been shown and described herein, it will be understood that such embodiments are provided by way of example only. Numerous variations, changes and substitutions will occur to those skilled in the art without departing from the scope of the invention. Accordingly, it is intended that the appended claims cover all such variations as fall within the scope of the invention.

What is claimed is:

1. A surgical guiding instrument for a surgical machining tool which is configured for machining vertebral bodies and has a distal tool end, the guiding instrument comprising a substantially elongated instrument body having a proximal and a distal end and defining a longitudinal axis, the instrument body comprising a guiding device for the machining tool, wherein the guiding device comprises a first guiding element in the form of a guiding sleeve having an axis offset from the longitudinal axis of the instrument body, the guiding sleeve comprising a first end, a second end and a guide surface inside the guiding sleeve, the guiding sleeve further comprising a through-opening, the through-opening extending from the first end of the guiding sleeve to the second end of the guiding sleeve, the through-opening having a cross sectional area that decreases as the through-opening extends from the first end toward the second end, forming a narrowed section in the guiding sleeve that creates a pivot axis offset from and perpendicular to the longitudinal axis of the instrument body to positively guide the machining tool along a superimposed translational-pivotal movement in which the machining tool moves in a nonparallel direction in relation to the guiding instrument.

2. The guiding instrument of claim 1, wherein the guiding device is arranged and constructed so as to enable a tip or a center of the distal tool end to be positively guided along a linear path curve.

3. The guiding instrument of claim 1, wherein the guiding device comprises a holder for the machining tool.

4. The guiding instrument of claim 3, wherein the holder is releasably connectable to the machining tool.

5. The guiding instrument of claim 3, wherein the holder comprises a clamping device for clamped connection to a machining tool.

6. The guiding instrument of claim 1, wherein the machining tool or a part thereof is displaceably and pivotably mountable on the first guiding element.

7. The guiding instrument of claim 1, wherein the first guiding element is arranged at the distal end or in the area of the distal end of the instrument body.

8. The guiding instrument of claim 1, wherein the guide surface is convexly curved in relation to a plane containing the longitudinal axis.

9. The guiding instrument of claim 1, wherein in a plane intersecting the longitudinal axis the guide surface is concavely curved in the direction towards the longitudinal axis.

10. The guiding instrument of claim 1, wherein the guide sleeve comprises a guide through-hole for at least a portion of the machining tool.

11. The guiding instrument of claim 10, wherein the guide through-hole comprises an inner wall surface, and the inner wall surface forms the guide surface.

12. The guiding instrument of claim 1, wherein the guiding device comprises a second guiding element for holding and guiding the machining tool on the instrument body, and the machining tool is mountable for sliding displacement and pivotal movement relative to the second guiding element.

13. The guiding instrument of claim 12, wherein a portion of the machining tool is mountable for sliding displacement on the second guiding element and pivotal movement about the pivot axis.

14. The guiding instrument of claim 12, wherein the second guiding element is arranged proximate to the proximal end of the instrument body.

15. The guiding instrument of claim 12, wherein the second guiding element comprises at least one first guiding member for guiding the machining tool or a part thereof along a curve defined by the second guiding element.

16. The guiding instrument of claim 15, wherein the second guiding element comprises at least one guiding body, and the at least one first guiding member is in the form of a guide groove arranged on the at least one guiding body.

17. The guiding instrument of claim 16, wherein two symmetrically arranged guiding bodies are provided.

18. The guiding instrument of claim 16, wherein the at least one guiding body comprises two or more guide grooves.

19. The guiding instrument of claim 16, wherein the at least one first guiding member is inclined relative to the longitudinal axis.

20. The guiding instrument of claim 16, wherein the holder comprises at least one second guiding member, and the at least one second guiding member is constructed so as to be movably mounted on the first guiding member.

21. The guiding instrument of claim 20, wherein the at least one second guiding member is a guiding projection which protrudes transversely or substantially transversely to the longitudinal axis and is shaped so as to enter into the at least one guide groove.

22. The guiding instrument of claim 21, wherein the second guiding element is arranged in spaced relationship to the first guiding element in the longitudinal direction.

23. The guiding instrument of claim 22, wherein a spacing between the first and second guiding elements is alterable.

24. The guiding instrument of claim 12, wherein the first and second guiding elements are arranged relative to each other and coordinated with each other such that a distal end of a machining tool is movable along a substantially straight line substantially parallel to the longitudinal axis.

25. The guiding instrument of claim 1, wherein an implant body for insertion into an intervertebral space between adjacent vertebral bodies of the vertebral column of a human being or an animal is provided at the distal end of the instrument body, and the implant body comprises two contact surfaces adapted for placement on the vertebral bodies.

26. The guiding instrument of claim 25, wherein the implant body is releasably connectable to the instrument body.

27. The guiding instrument of claim 25, wherein the contact surfaces are inclined relative to each other about an angle of inclination.

28. The guiding instrument of claim 25, wherein a set of implant bodies is provided, and the implant bodies of the set have a different size and/or a different angle of inclination of the contact surfaces relative to each other and/or a different spacing of the contact surfaces from each other.

29. The guiding instrument of claim 25, wherein at least one guide groove is arranged in one of the two contact surfaces on the implant body so as to extend parallel or substantially parallel to the longitudinal axis of the instrument body.

30. The guiding instrument of claim 25, wherein a stop device is provided for limiting a penetration depth of the implant body into the intervertebral space.

31. The guiding instrument of claim 30, wherein the stop device comprises at least one projection protruding transversely or substantially transversely to the longitudinal axis of the instrument body.

32. The guiding instrument of claim 30, wherein the stop device is releasably connectable to the implant body or to the instrument body.

33. The guiding instrument of claim 30, wherein the stop device comprises a carrier, and the implant body or the instrument body comprises a guiding device for the carrier for guiding a movement of the carrier relative to the implant body or to the instrument body substantially parallel to the longitudinal axis.

34. The guiding instrument of claim 33, wherein the guiding device comprises at least one guiding bar protruding in a proximal direction on the implant body, and the carrier is displaceably mounted on the at least one guiding bar.

35. The guiding instrument of claim 33, wherein the stop device comprises a stop member, and a spacing between the stop member and the carrier is alterable.

36. The guiding instrument of claim 33, wherein the carrier carries the at least one projection.

37. The guiding instrument of claim 1, wherein a grip part is provided at the proximal end of the instrument body.

38. The guiding instrument of claim 37, wherein the grip part is releasably connectable to the instrument body.

39. The guiding instrument of claim 37, wherein the grip part and the instrument body extend at an angle relative to each other.

40. The guiding instrument of claim 1, wherein the guiding instrument is constructed symmetrically in relation to a mirror plane containing the longitudinal axis.

41. Surgical instrumentation comprising at least one surgical machining tool which is configured for machining vertebral bodies and has a distal tool end, and at least one surgical guiding instrument for the at least one surgical machining tool, the guiding instrument comprising a substantially elongated instrument body having a proximal end and a distal end and defining a longitudinal axis, the instrument body comprising a guiding device for the machining tool, wherein the guiding device comprises a guiding sleeve having an axis offset from the longitudinal axis of the instrument body, the guiding sleeve comprising a first end, a second end and a guide surface inside the guiding sleeve, the guiding sleeve further comprising a through-opening, the through-opening extending from the first end of the guiding sleeve to the second end of the guiding sleeve, the through-opening having a cross sectional area that decreases as the through-opening extends from the first end toward the second end, forming a narrowed section in the guiding sleeve that creates a pivot axis offset from and perpendicular to the longitudinal axis of the instrument body to positively guide the machining tool along a superimposed translational-pivotal movement in which the machining tool moves in a nonparallel direction in relation to the guiding instrument.

42. The instrumentation of claim 41, wherein the guiding device of the at least one surgical guiding instrument is arranged and constructed so as to enable a tip or a center of the distal tool end to be positively guided by it along a linear path curve.

43. The instrumentation of claim 41, wherein the at least one machining tool is a milling tool with an elongated shaft, and the distal tool end is a rotatable milling head.

44. The guiding instrument of claim 1 wherein the annular guide surface inside the guiding sleeve has a circular ring shape.

45. The instrumentation of claim 41, wherein the annular guide surface inside the guiding sleeve has a circular ring shape.

* * * * *